United States Patent [19]

Hassler et al.

[11] Patent Number: 4,865,041
[45] Date of Patent: Sep. 12, 1989

[54] LITHOTRIPTER HAVING AN ULTRASOUND LOCATING SYSTEM INTEGRATED THEREWITH

[75] Inventors: Dietrich Hassler, Uttenreuth; Erhard Schmidt, Erlangen, both of Fed. Rep. of Germany

[73] Assignee: Siemens Aktiengesellschaft, Berlin and Munich, Fed. Rep. of Germany

[21] Appl. No.: 151,324

[22] Filed: Feb. 1, 1988

[30] Foreign Application Priority Data

Feb. 4, 1987 [DE] Fed. Rep. of Germany ....... 3703332

[51] Int. Cl.⁴ .............................................. A61B 17/22
[52] U.S. Cl. ........................... 128/660.03; 128/24 A; 128/328
[58] Field of Search ...................... 128/24 A, 328, 660, 128/660.03

[56] References Cited

U.S. PATENT DOCUMENTS 4,526,168  7/1985  Hassler et al. ..................... 128/24 A
4,669,483  6/1987  Hepp et al. ......................... 128/328

FOREIGN PATENT DOCUMENTS 0221592  5/1987  European Pat. Off. .
3328039  2/1985  Fed. Rep. of Germany .
3617032  1/1987  Fed. Rep. of Germany ...... 128/328

*Primary Examiner*—Ruth S. Smith
*Attorney, Agent, or Firm*—Hill, Van Santen, Steadman & Simpson

[57] ABSTRACT

A lithotripter for disintegrating a calculus in the body of a patient has a shock wave source which generates shock wave pulses which are focussed into coincidence with the calculus by an acoustic lens. The lithotripter has an ultrasound locating system integrated therewith, the locating system having a mechanically pivotable element for undertaking a sector scan of a portion of the patient to identify the position of the calculus therein. The pivotable element may be an ultrasound transducer, or may be an acoustic mirror which reflects ultrasound signals from a transducer disposed laterally of the mirror, as well as reflecting echo signals from the calculus back to the transducer. The rotational axis of the pivotable element is disposed perpendicularly on the central axis of the acoustic lens. A synchronization unit controls triggering of the shock wave pulses so that the pulses are generated only when the pivotable element is in a position which presents the smallest obstruction in the direction of propagation of the pulses to the calculus. The position of the calculus can be observed during the entire lithotripsy treatment, so that if the calculus shifts out of the focus zone of the acoustic lens, this is recognized in the ultrasound image and a re-positioning of the focus can be undertaken. The pivotable element can be disposed preceding or following the acoustic lens, as seen in the direction of shock wave pulse propagation. When the pivotable element is disposed preceding the acoustic lens, the fan-shaped ultrasound locating beam is re-shaped by the acoustic lens into a parallel scan beam, so that the path of the shock wave pulse can be completely monitored.

24 Claims, 6 Drawing Sheets

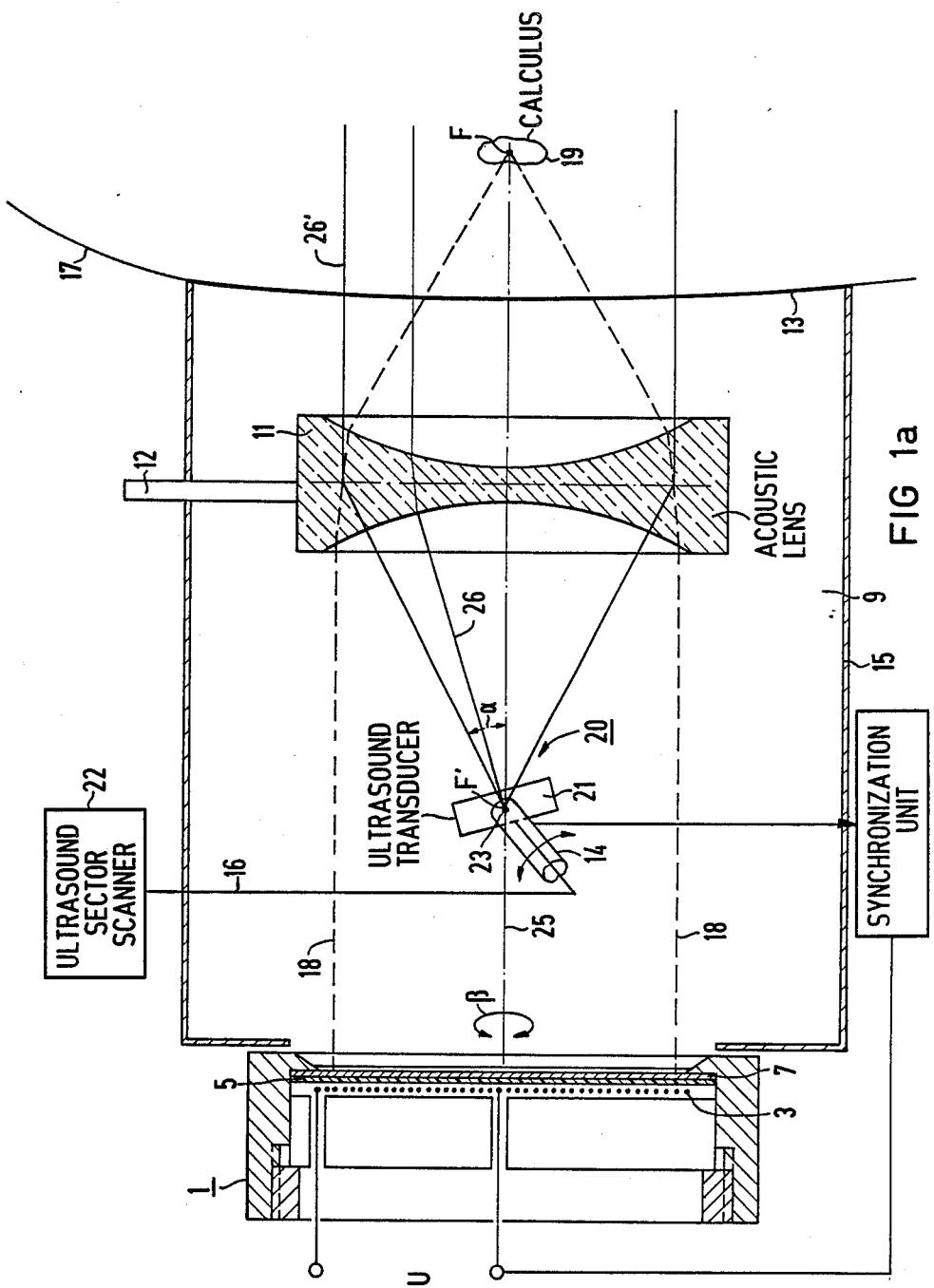

LITHOTRIPTER HAVING AN ULTRASOUND LOCATING SYSTEM INTEGRATED THEREWITH

BACKGROUND OF THE INVENTION

1. Field of the Invention

The present invention relates to lithotripsy devices, and in particular to such devices combined with a means for locating the calculus to be disintegrated in the body of a patient.

2. Description of the Prior Art

A shock wave device for disintegrating a calculus in the human body is generally described, for example, in German OS No. 33 28 039. A shock wave tube is used as the shock wave source. The shock wave tube has an electrical coil, an insulating foil, and a copper membrane arranged in sequence. When a current pulse is applied to the coil, eddy currents are generated in the membrane, causing the membrane to be rapidly repelled from the coil. A shock wave is formed in the adjacent transmission medium, such as water. The shock wave is focussed by an acoustic lens having a focal point disposed in the calculus of the patient after a suitable positioning procedure. The calculus may be, for example, a kidney stone.

Locating the position of the calculus in the body of the patient is of great significance to the degree of therapeutic success, as well as for decreasing the load on the patient during therapy. The chances for successful therapy increase, and the load on the patient decrease, as the targeting becomes more precise. It is known to undertake such locating using x-ray devices. A disadvantage of such conventional locating means, however, is that the position of the calculus cannot be monitored during the complete shock wave treatment, because this would result in an undesireable x-radiation load on the patient. X-ray images are therefore recorded only from time to time during therapy to monitor the position of the calculus.

For continuously monitoring the calculus position, it is known to use an ultrasound system as the locating means. For example, German Pat. No. 34 27 001 corresponding to U.S. Pat. No. 4,669,483 discloses a locating and positioning method wherein the calculus is located with an ultrasound oscillator, prescribed identification marks are set, and the calculus and the focal point of the shock wave system are subsequently mechanically brought into coincidence.

It is also known from German OS No. 31 19 295 corresponding to U.S. Pat. No. 4,526,168 to undertake locating of the calculus using the shock wave source itself. In the system described therein, the shock wave source is an arrangement of a plurality of piezo electric transducer elements. This method, however, can be used only given shock wave sources wherein the shock wave pulse is produced using such piezo electric elements.

SUMMARY OF THE INVENTION

It is an object of the present invention to provide a lithotripter having an ultrasound locating means integrated therewith for continuously monitoring the position of the calculus, the ultrasound locating means being integrable with the lithotripter regardless of the type of shock wave source used.

It is another object of the present invention to provide such a lithotripter which permits the calculus position to be monitored during the action of the shock wave pulses thereon.

The above objects are achieved in accordance with the principles of the present invention in a lithotripter having an ultrasound locating system, such as an ultrasound sector scanner, integrated therewith, the ultrasound locating system having a pivotable element disposed in the lithotripter which is rotatable about an axis perpendicular to the central axis of the acoustic lens. The pivotable element may be an ultrasound transducer or may be a mirror, which reflects ultrasound radiation from an ultrasound transducer disposed laterally of the mirror, and which also reflects ultrasound echo signals from the calculus back to the ultrasound transducer.

The pivotable element may be disposed preceding or following the acoustic lens, as seen in the direction of propagation of the shock wave pulses.

In the lithotripter disclosed and claimed herein, identification of the position of the calculus can be undertaken in real time, independently of the type of shock wave source which is used. The calculus can be continuously observed, so that any change in position such as, for example, due to breathing of the patient, can be retracked for the entire duration of the treatment.

The pivotable element in a preferred embodiment can be rotated through an angle of +90° through −90°. A synchronization unit may be provided which controls the triggering time of each shock wave pulse based on the angular position of the ultrasound transducer or acoustic mirror. By the operation of the synchronization unit, the shock wave pulse is triggered when the transducer or mirror has its smallest face directed toward the shock wave generator, so as to present the smallest obstruction to the propagation of shock waves from the generator to the calculus. The shock wave pulse is only slightly attenuated when the transducer or mirror is in this position.

As noted above, the means for focussing the shock wave pulses may be an acoustic lens. If such an acoustic lens is used, the pivotable element can be disposed in the first focus of the lens, i.e., the focus on the side of the lens closest to the source of the shock wave pulse. The pivotable element emits or reflects fan-shaped ultrasound locating pulses from this first focus as a sensing beam, these pulses being incident on the lens surface. The lens may, for example, be a double concave lens. The lens reshapes the sensing beam into a parallel scan beam. The parallel scan beam covers the region of the patient in which the calculus lies, and a relatively large portion of the surrounding environment. If, for example, the position of the focus of the shock wave pulses is mixed with the ultrasound image, movement of the calculus out of coincidence with the focus can be observed without difficulty. This is possible in the real time operation during the entire lithotripsy treatment of the patient.

DESCRIPTION OF THE DRAWINGS

FIG. 1a is a side sectional view of a second embodiment of a lithotripter constructed in accordance with the principles of the present invention.

DESCRIPTION OF THE PREFERRED EMBODIMENTS

Figure 1:
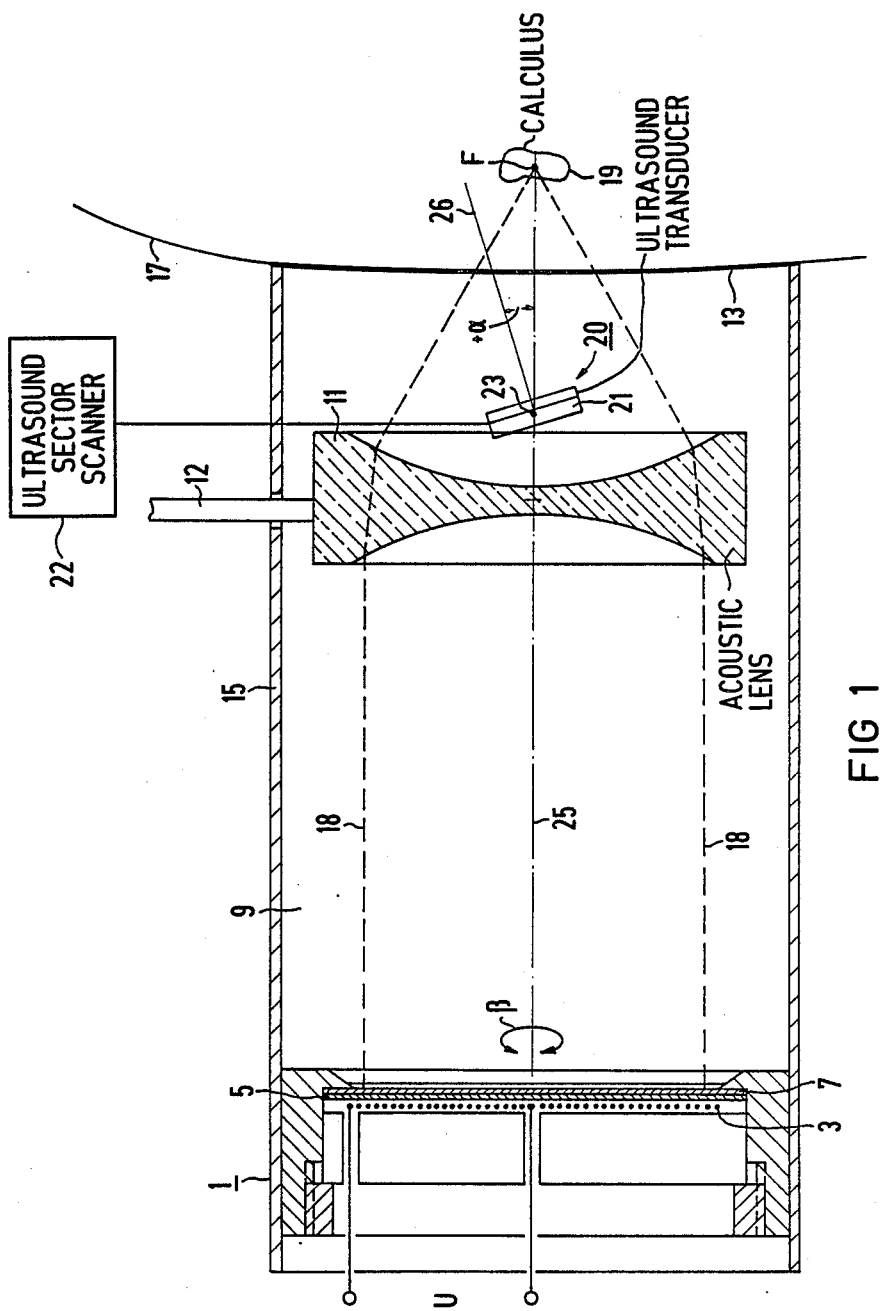
FIG. 1 is a side sectional view of a first embodiment of a lithotripter constructed in accordance with the principles of the present invention.

A lithotripter constructed in accordance with the principles of the present invention is shown in FIG. 1 in the form of a shock wave tube. The lithotripter includes a shock wave source generally referenced at 1, which has a flat electrical coil 3 in a helical configuration with a metallic membrane 7 (consisting of, for example, copper) disposed in front thereof and separated therefrom by an insulating foil 5. The coil 3 may be charged with a voltage pulse U. The metallic membrane 7 is followed in the direction of shock wave propagation by an approach path 9. A means for focussing the shock waves in the form of an acoustic lens 11 is supported by a mount 12 in the approach path 9. The approach path 9 is terminated by a coupling membrane 13. The lithotripter is contained within a cylindrical tube 15 with one end closed by the shock wave source 1 and the opposite end closed by the coupling membrane 13. The interior of the lithotripter is filled with a coupling fluid, such as water.

The coupling membrane 13 is applied to the skin of a patient 17. The shock wave source 1 is thereby positioned so that the focus F of the acoustic lens 11 coincides with the position of a calculus 19, for example, a kidney stone. The shock wave path is illustrated by the dashed lines 18.

Upon the application of a voltage pulse U to the coil 3, the metallic membrane 7 is rapidly repelled therefrom, generating a shock wave pulse which is transmitted through the coupling medium and is focussed by the acoustic lens 11 to disintegrate the calculus 19.

As seen in the direction of propagation of the shock waves, a pivotable element 20, which is part of an ultrasound sector scanner 22, is disposed within the lithotripter following the acoustic lens 11. In the embodiment of FIG. 1, the pivotable element is an ultrasound transducer 21. The transducer 21 pivots or rotates about an axis 23 disposed perpendicularly with respect to the central axis 25 of the acoustic lens 11. The ultrasound transducer 21 is a vibrating transducer having an emission and reception direction 26 moveable by an angle $\alpha$ on both sides of the central axis 25. The total angle of movement is preferably 90° on each side of the central axis 25, thus a mounting to a total angle of 180°. Rotation of the transducer 21 generates a sector scanning beam proceeding from a point which lies on the central axis 25 between the acoustic lens 11 and the membrane 13.

As shown in the embodiment of FIG. 1a, the pivotable element of the ultrasound sector scanning system may alternatively be disposed preceding the acoustic lens 11, as seen in the direction of shock wave propagation. This element, again generally referenced at 20, may also be an ultrasound transducer 21 rotatable about an axis 23 and having an emission and reception direction 26 disposed at the angle $\alpha$ relative to the central axis 25.

Whether disposed in front of or behind the acoustic lens 11, the pivotable element 20 may be mechanically rotated about the axis 23 by a shaft 14, shown in FIG. 1a, but applicable to all of the embodiments, extending to the exterior of the lithotripter. Rotation of the shaft 14, as indicated by the curved double arrow, is controlled by the ultrasound sector scanner 22. The sector scanner 22 also includes answerback elements of the type known in the art. The electrical leads for the pivotable element 20 may be accommodated within the shaft 14, as schematically indicated by the cable 16.

If the pivotable element 20 is an ultrasound transducer, the transducer is of conventional construction in operation. Means may also be provided for rotating the pivotable element 20 around the central axis 25, as schematically indicated by the circular double arrow $\beta$.

A synchronization unit 24, again shown only in FIG. 1a but applicable to all embodiments, may also be provided which synchronizes the triggering time of each shock wave pulse with the angular position of the pivotable element 20. The synchronization unit 24 identifies the angular position of the element 20 relative to the central axis 25 from the angular position of the shaft 14. The synchronization unit 24 will enable triggering of a shock wave pulse only when the element 20 is positioned with at $\alpha$ at $\pm 90°$, so that the smallest face of the element 20 is facing the shock wave source 1. The element 20 thus presents the smallest obstruction to the shock waves at this position. As a result, the shock wave pulse will be only slightly shadowed by the element 20, and it will have a minimal effect on the disintegrating capability of the shock wave pulse. The disintegrating action of the shock wave pulse on the element 20 is also minimized in this manner.

Instead of consisting of a single ultrasound transducer 21 the pivotable element 20 may consist of an array of ultrasound transducer elements, such as an annular array, which in combination have an emission direction 26, again positionable relative to the central axis 25 by rotation of the element about the axis 23.

Figure 2:
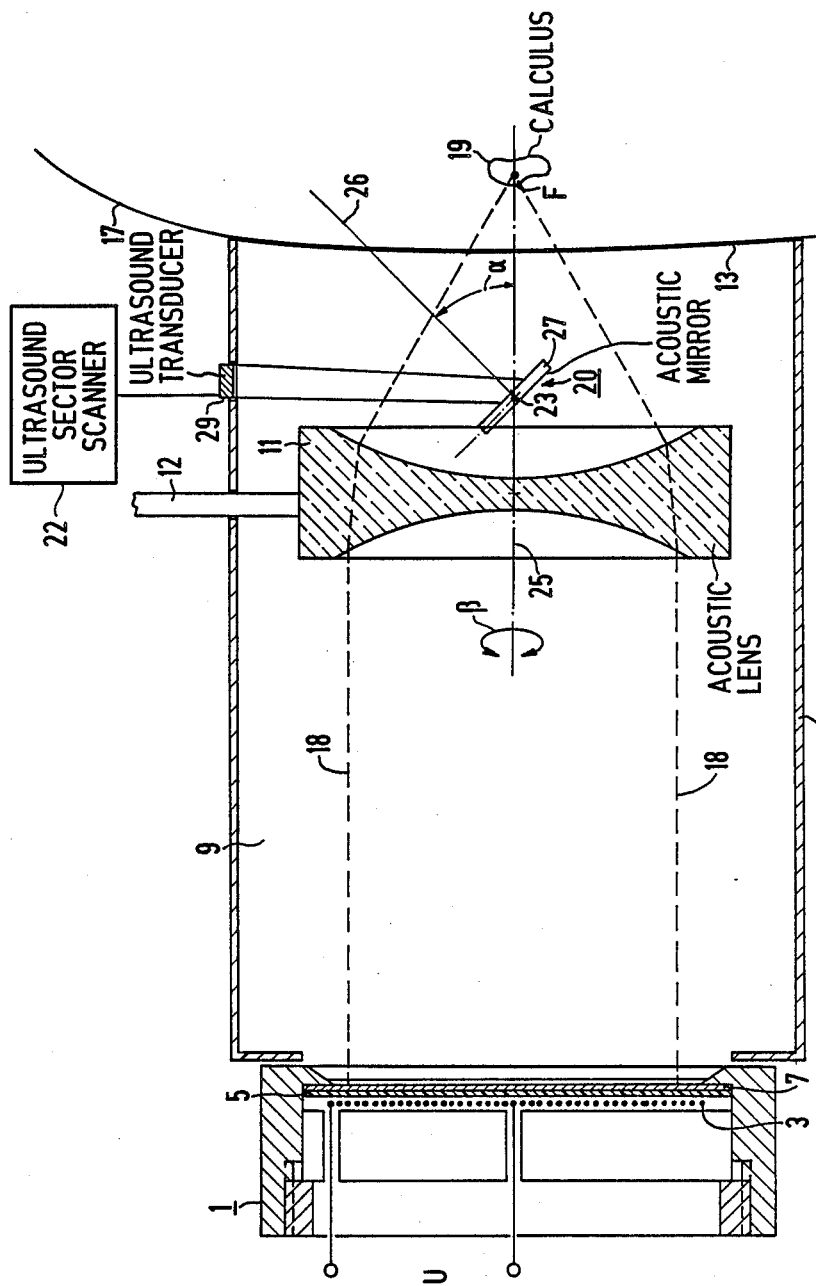
FIG. 2 is a side sectional view of a third embodiment of a lithotripter constructed in accordance with the principles of the present invention.

In another embodiment shown in FIG. 2, the pivotable element 20 may be an ultrasound mirror 27, rotatable around the axis 23 in the same manner described above in connection with the embodiment of FIG. 1a. In the embodiment of FIG. 2, the ultrasound mirror 27 is disposed following the acoustic lens 11 in the direction of shock wave propagation, and is irradiated by ultrasound signals from a laterally disposed ultrasound transducer 29, which is a part of the ultrasound sector scanner 22. The transducer 29 may be mounted, for example, to the wall of the tube 15. Means may be provided for rotating the acoustic mirror 27 together with the transducer 29 around the central axis 25, as again schematically indicated by the double arrow $\beta$. The acoustic mirror 27 reflects ultrasound locating pulses emitted by the transducer 29 toward the calculus 19, and also reflects ultrasound echo pulses from the calculus 19 back to the transducer 29. As in the embodiment of FIG. 1a a synchronization unit may be provided to enable triggering of shock wave pulses only when the acoustic mirror 27 has its smallest face oriented toward the shock wave source 1, however, such a synchronization unit is not shown in the drawing of FIG. 2 for clarity.

By rotating the pivotable element 20 in both embodiments of FIG. 1 and FIG. 2 around the central axis 25 through the angle $\beta$, a cone inside the patient 17, as opposed to only a plane, can be scanned. By selectively varying the angles α and β in combination, other types of scan formats can be obtained.

In the embodiments of FIGS. 1 and 2, wherein the pivotable element 20 is disposed between the acoustic lens 11 and the membrane 13, image disturbances due to multiple reflections are minimized. If the acoustic lens 11 is adjusted to a different distance from the coupling membrane 13 to bring the focus F into coincidence with the calculus 19, the pivotable element 20 should be maintained at a fixed distance from the membrane 13.

The embodiments of FIGS. 1, 1a and 2 (as well as the embodiments discussed below) permit tracking the position of the calculus 19 during the entire lithotripsy treatment. Potential movements of the calculus 19 out of coincidence with the focus F can be observed and corrected by readjusting the position of the shock wave source 1, or by other means such as the use of a flexible coupling sack.

Figure 4:
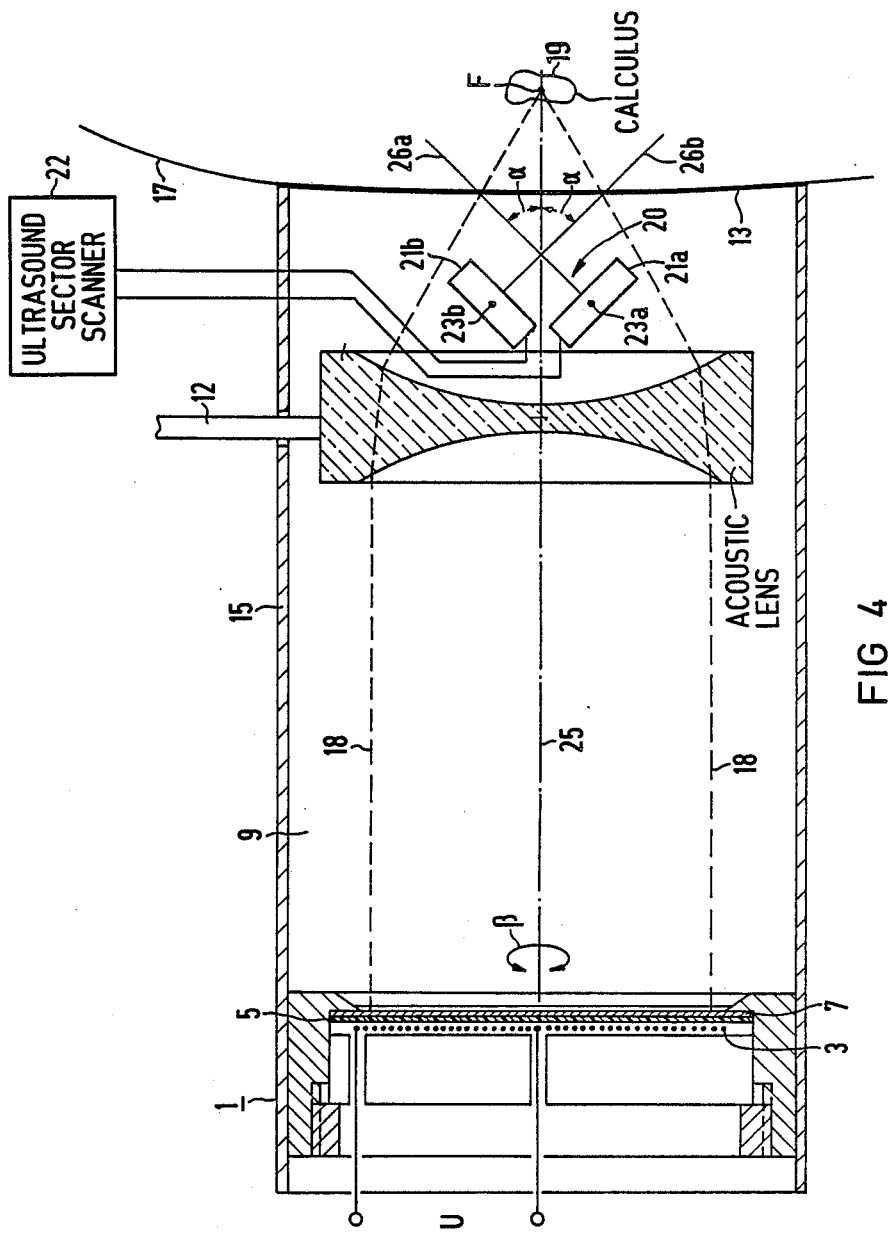
FIG. 4 is a side sectional view of a fifth embodiment of a lithotripter constructed in accordance with the principles of the present invention.
Figure 5:
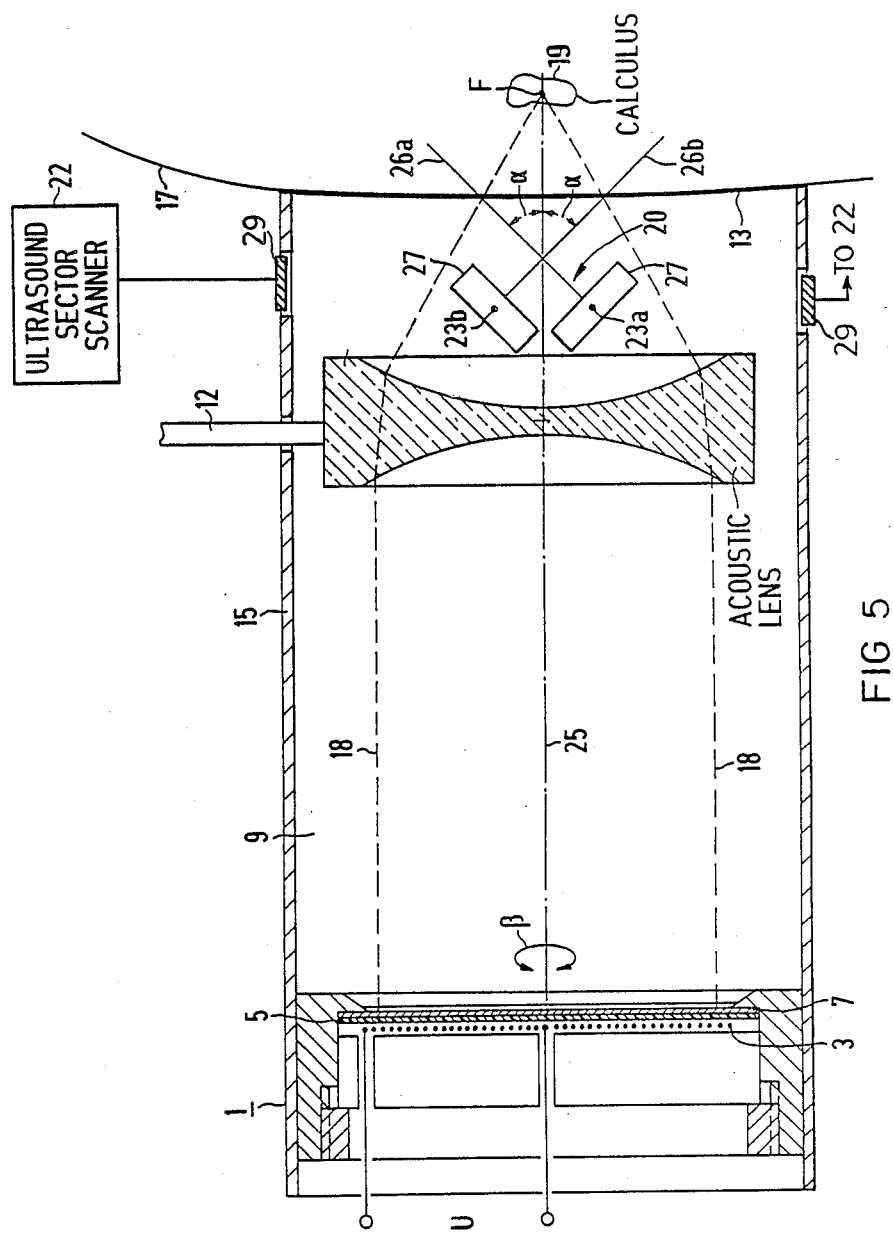
FIG. 5 is a side sectional view of a sixth embodiment of a lithotripter contructed in accordance with the principles of the present invention.

In a further embodiment shown in FIG. 4, the pivotable element 20 consists of two ultrasound transducers 21a and 21b disposed symmetrically and slightly eccentrically relative to the central axis 25. Each transducer 21a and 21b scans a plane, with the planes being disposed perpendicularly relative to each other and being evaluated simultaneously. Again, each transducer 21a or 21b is rotatable about a respective axis 23a and 23b extending perpendicularly relative to the central axis 25. Rotation of the transducers 21a and 21b ensues as described above in connection with FIG. 1a by means of a mechanical shaft, and a synchronization unit as also described in connection with FIG. 1 may also be provided to control triggering of the shock wave pulses relative to the angular positions of the transducers 21a and 21b. In the embodiment of FIG. 4, the pivotable element 20 may alternatively consist of two pivotable mirrors, corresponding to the embodiment of FIG. 2 as shown in FIG. 5, in which case each mirror will have an associated ultrasound transducer disposed laterally with respect thereto. Each mirror or transducer 21a and 21b can also be rotated around the central axis 25, as again schematically indicated by the circular arrow β.

Figure 3:
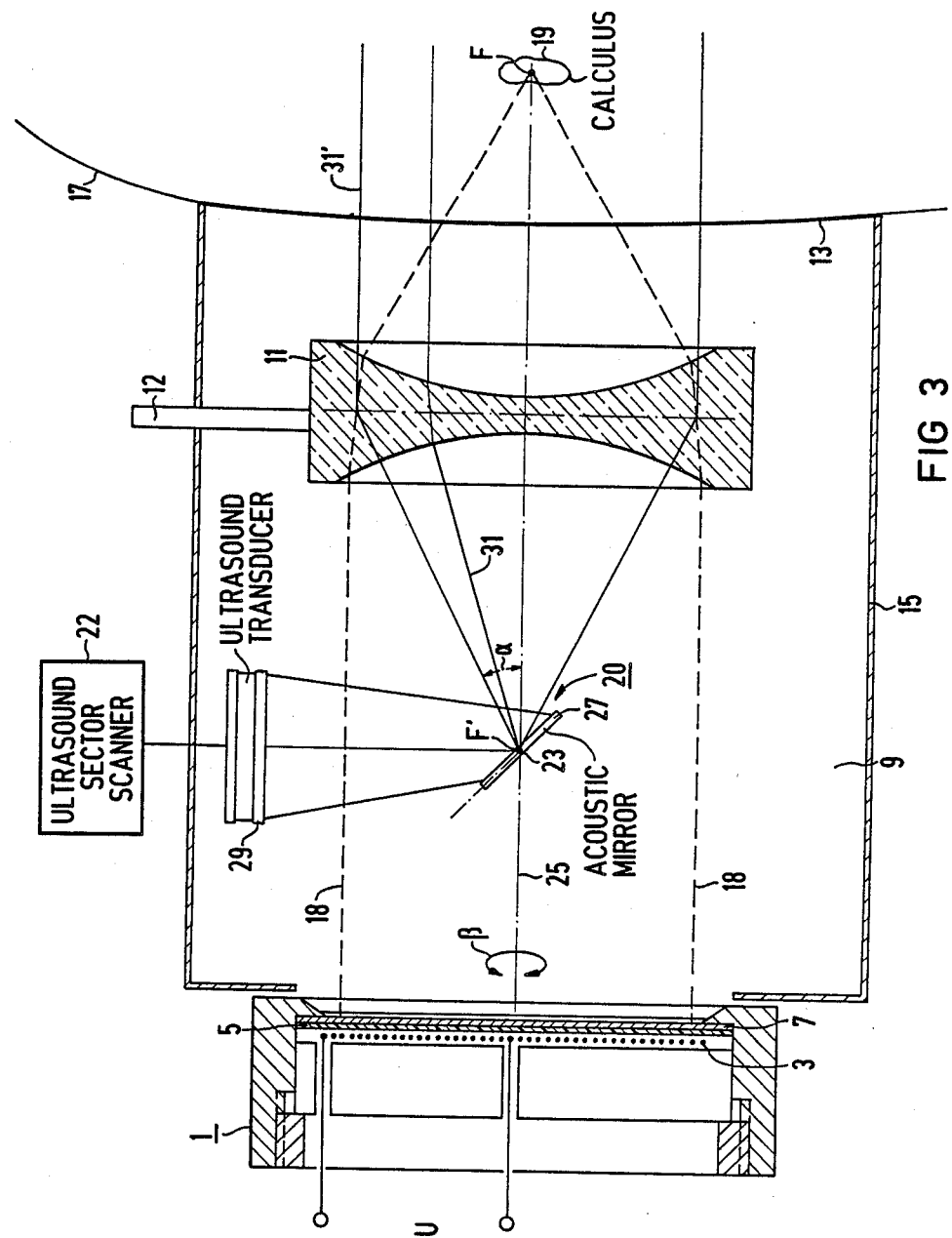
FIG. 3 is a side sectional view of a fourth embodiment of a lithotripter constructed in accordance with the principles of the present invention.

Another embodiment is shown in FIG. 3, wherein the pivotable element 20 is again an acoustic mirror 27, with an associated ultrasound transducer 29. In this embodiment, the pivotable element 20 is disposed in front of the acoustic lens 11, as seen in the direction of shock wave propagation. The pivoting axis 23 of the mirror 27 preferably coincides with the first focus F' of the acoustic lens 11. As described in connection with the embodiment of FIG. 2, the acoustic mirror 27 is irradiated with ultrasound locating pulses from the transducer 29. In the embodiment of FIG. 3, however, because the mirror 27 is disposed in front of the acoustic lens 11 at the first focus F', the sector scan, indicated at 31, is converted into a parallel scan, indicated at 31', by the operation of the acoustic lens 11.

The same result occurs in the embodiment of FIG. 1a, wherein the pivotable element 20 is an ultrasound transducer 21, having the aforementioned axis of rotation 23 coincident with the first focus F' In this embodiment, the sector scan indicated at 26 is converted into a parallel scan, indicated at 26'.

The acoustic mirror 27 in the embodiment of FIG. 3 is mechanically rotated as described above in connection with FIG. 1a, and a synchronization unit can also be provided in the embodiment of FIG. 3 in the manner described above to enable triggering of the shock wave pulses only when the smallest face of the mirror 27 is oriented toward the shock wave source 1.

Additionally, in both of the embodiments of FIG. 1a and FIG. 3, two transducers or two mirrors disposed symmetrically and slightly eccentrically with respect to the central axis 25 may be used, as described in connection with FIG. 4.

An advantage of the embodiments shown in FIG. 1a and 3, wherein the pivotable element 20 is disposed in front of the acoustic lens 11, is that substantially the entire approach path for the shock wave pulse can be monitored, rather than simply a localized area around the calculus 19. Optimization of the coupling or the acoustic irradiation direction can thus be undertaken as needed. For this purpose, it is useful to mix the signals corresponding to the path of the shock wave pulse into the B-image of the ultrasound system. Multiple echos, which may possibly be produced inside the lens 11, and which could lead to double images, can be suppressed by suitable coating of the acoustic lens 11. Another alternative in the embodiments of FIGS. 1a and 3 is to place the mirror 27 or the transducer 21 in front of or behind the first focus F' so that respectively a divergent scan or a convergent scan can be produced, instead of the above-described parallel scan.

Although modifications and changes may be suggested by those skilled in the art it is the intention of the inventors to embody within the patent warranted hereon all changes and modifications as reasonably and properly come within the scope of their contribution to the art.

We claim as our invention:

1. A lithotripter for disintegrating a calculus in the body of a patient comprising:
   a shock wave tube;
   means attached at one of said shock wave tube for generating shock wave pulses;
   a flexible membrane closing an opposite end of said shock wave tube and defining a volume in combination with said shock wave tube and said means for generating shock wave pulses;
   a shock-wave conducting medium filling said volume; means in said volume for focussing said shock wave pulses at a point coincident with said calculus, said means for focussing having a central axis;
   an ultrasound locating means for identifying the position of said calculus in said body, said ultrasound locating means including a pivotable means disposed in said lithotripter for directing ultrasound locating signals to, and receiving
   ultrasound echo signals from, said calculus; and
   means for mechanically pivoting said pivotable means around an axis perpendicular to said central axis.

2. A lithotripter as claimed in claim 1, wherein said pivotable means is an ultrasound transducer.

3. A lithotripter as claimed in claim 1, wherein said pivotable means is an ultrasound transducer array.

4. A lithotripter as claimed in claim 1, wherein said pivotable means is an acoustic mirror, and further comprising an ultrasound transducer disposed in said shock wave tube laterally of said acoustic mirror such that said locating signals and said echo signals are also directed to and received from said ultrasound transducer.

5. A lithotripter as claimed in claim 1, wherein said pivotable means consists of two pivotable elements respectively disposed on opposite sides of said central axis, and wherein said means for pivoting includes means for pivoting each pivotable element about a respective axis perpendicular to said central axis, and each pivotable element having a transmission/reception direction, the transmission/reception directions for the two pivotable elements being perpendicularly disposed.

6. A lithotripter as claimed in claim 5, wherein said axes about which said pivotable elements are respectively pivotable are parallel.

7. A lithotripter as claimed in claim 5, wherein each pivotable element is an ultrasound transducer.

8. A lithotripter as claimed in claim 5, wherein each pivotable element is an ultrasound transducer array.

9. A lithotripter as claimed in claim 5, wherein each pivotable element is an acoustic mirror, and further comprising two ultrasound transducers respectively associated with each acoustic mirror, said ultrasound transducers being respectively disposed laterally of the associated acoustic mirror, and each acoustic mirror respectively directing and receiving ultrasound locating signals and echo signals to and from the associated transducer.

10. A lithotripter as claimed in claim 5, wherein said pivotable elements are disposed following said means for focussing in the direction of shock wave pulse propagation.

11. A lithotripter as claimed in claim 1, wherein said pivotable means is disposed following said means for focussing in the direction of shock wave pulse propagation.

12. A lithotripter as claimed in claim 10, wherein said pivotable means is disposed a fixed distance from said flexible membrane.

13. A lithotripter as claimed in claim 1, wherein said pivotable means is disposed preceding said means for focussing in the direction of shock wave pulse propagation.

14. A lithotripter as claimed in claim 13, wherein said means for focussing has a focal point preceding said means for focussing in the direction of shock wave propagation, and wherein said axis about which said pivotable means is pivotable extends through said focal point.

15. A lithotripter as claimed in claim 1, wherein said means for mechanically pivoting said pivotable means pivots said pivotable means through an angle of +90° relative to said central axis.

16. A lithotripter as claimed in claim 1, wherein said means for mechanically pivoting said pivotable means includes a rotary shaft extending laterally through said shock wave tube and attached to said pivotable means.

17. A lithotripter as claimed in claim 16, wherein said pivotable means has at least one electrical line connected thereto, and wherein said electrical line is contained within said shaft.

18. A lithotripter as claimed in claim 1, wherein said pivotable means has a smallest face, and wherein said pivotable means is pivotable by said means for mechanically pivoting such that said smallest face is oriented toward said means for generating shock wave pulses, and further comprising synchronization means connected to said means for mechanically pivoting and to said means for generating shock wave pulses for enabling triggering of said shock wave pulses only when said smallest face of said pivotable means is oriented toward said means for generating shock wave pulses.

19. A lithotripter as claimed in claim 1, further comprising means for rotating said pivotable means around said central axis.

20. A lithotripter for disintegrating a calculus in the body of a patient comprising:
housing;
means attached to said housing for generating shock wave pulses;
means in said housing for focussing said shock wave pulses at a focal point following said means for focussing in direction of shock wave pulses propagation coincident with said calculus, said means for focussing having a central axis and a further focal point preceding said means for focussing in the direction of shock wave pulse propagation;
an ultrasound locating means for identifying the position of said calculus in said body, said ultrasound locating means including an ultrasound element disposed in said housing at said further focal point, said ultrasound locating signals to, and receiving ultrasound echo signals from, said calculus through said means for focussing; and
means for mechanically pivoting said ultrasound element around an axis perpendicular to said central axis and extending through said further focal point.

21. A lithotripter as claimed in claim 20, wherein said ultrasound element is an ultrasound transducer.

22. A lithotripter as claimed in claim 20, wherein said ultrasound element is an ultrasound transducer array.

23. A lithotripter for disintegrating a calculus in the body of a patient comprising:
means attached at one end of said shock wave tube a shock wave tubes for generating shock wave pulses; a flexible membrane closing an opposite end of said shock wave tube and defining a volume in combination with said shock wave tube and said means for generating shock wave pulses;
a shock wave conduting medium filling said volume;
means in said volume for focussing said shock wave pulses at a point coincident with said calculus, said means for focussing having a central axis;
an ultrasound locating means for identifying the position of said calculus in said body, said ultrasound locating means, including an acoustic mirror disposed in said Volume with said central axis extending through said acoustic mirror, and an ultrasound transducer disposed laterally of said acoustic mirror, said acoustic mirror and said ultrasound transducer being respectively disposed relative to said calculus such that said acoustic mirror reflects ultrasound locating signals generated by said ultrasound transducer toward said calculus, and said acoustic mirror reflects ultrasound echo signals from said calculus toward said ultrasound transducer, said acoustic mirror being disposed following said means for focussing in the direction of shock wave pulse propagation; and
means for mechanically pivoting said acoustic mirror around an axis perpendicular to and extending through said central axis.

24. A lithotripter for disintegrating a calculus in the body of a patient comprising:
means attached to said housing for generating shock wave pulses;
means, in said housing for focussing said shock wave pulses at a focal point following said means for focussing in the direction of shock wave pulse propagation coincident with said calculus, said means for focussing having a central axis and having a further focal point preceding said means for focussing in the direction of shock wave pulse propagation;

an ultrasound locating means for identifying the position of said calculus in said body, said ultrasound locating means including an acoustic mirror disposed at said further focal point with said central axis extending through said acoustic mirror, and an ultrasound transducer disposed laterally of said acoustic mirror, said acoustic mirror reflecting ultrasound locating signals from said ultrasound transducer through said focussing means to a region of said patient surrounding said calculus, and reflecting ultrasound echo signals from said region of said patient after passing through said means for focussing toward said ultrasound transducer; and means for mechanically pivoting said acoustic mirror around an axis perpendicular to said central axis and extending through said further focal point.

* * * * *